United States Patent [19]

Reich et al.

[11] 4,245,051

[45] Jan. 13, 1981

[54] HUMAN SERUM PLASMINOGEN ACTIVATOR

[75] Inventors: Edward Reich, New York; Arabinda Guha, Pelham Manor; Wolf-Dieter Schleuning, New York, all of N.Y.

[73] Assignee: Rockefeller University, New York, N.Y.

[21] Appl. No.: 891,808

[22] Filed: Mar. 30, 1978

[51] Int. Cl.³ .................... C12N 9/48; A61K 35/16
[52] U.S. Cl. .................. 435/212; 260/112 B; 424/101
[58] Field of Search ............ 260/112 B; 424/101; 435/212, 215

[56] References Cited

U.S. PATENT DOCUMENTS

| | | | |
|---|---|---|---|
| 3,555,000 | 1/1971 | Wagner | 260/112 B |
| 3,808,124 | 4/1974 | Dziobkowski et al. | 260/112 B X |
| 3,865,692 | 2/1975 | Holleman et al. | 424/101 X |
| 3,904,480 | 9/1975 | Hull et al. | 195/66 B |
| 3,943,245 | 3/1976 | Silverstein | 260/112 B X |
| 3,998,947 | 12/1976 | D'Hinterland et al. | 424/101 X |

OTHER PUBLICATIONS

Summaria et al., *J. Biol. Chem.*, vol. 251, No. 18, (1976), pp. 5810–5813.
Fletcher et al., *J. Lab. and Clinical Med.*, vol. 65, No. 5, (1965), pp. 713–731.
Laemmli, *Nature*, vol. 227, (1970), pp. 680–685.
Converse et al., *Science*, vol. 189, (1975), pp. 469–472.

*Primary Examiner*—Lionel M. Shapiro
*Attorney, Agent, or Firm*—Haight, Rosfeld, Noble & Santa Maria

[57] ABSTRACT

A plasminogen proactivator and a corresponding activator has been isolated from mammalian and avian, especially human, plasma which is characterized within a given species as a single, electrophoretically and immunologically homogeneous protein. The activator acts as a catalyst to initiate fibrinolytic activity in plasma and is therefore useful in controlling clotting which occurs, e.g. in venous thrombosis or arterial occulsion, and in diagnosing conditions which predispose to thromboembolic phenomena. The proactivator has a long useful in vivo half life and can be used to provide a reservoir for maintaining the fibrolytic potential of blood.

4 Claims, No Drawings

HUMAN SERUM PLASMINOGEN ACTIVATOR

BACKGROUND OF THE INVENTION

This invention relates to a plasminogen proactivator and activator which can be isolated from mammalian and avian plasma, concentrated plasma protein fractions (such as Cohn fractions) or from corresponding cell culture fluids; to methods for the isolation and purification thereof; to pharmaceutical and diagnostic methods and compositions for the use thereof; to the production of antisera thereto; and to the use of such antisera in purification of the plasminogen proactivator and activator and in measurement of plasminogen activator levels in the blood and body fluids.

As thrombin, which converts the soluble fibrinogen of the blood into insoluble fibrin, exists in the form of a proenzyme, i.e. prothrombin, so also does plasmin, the proteolytic enzyme which lyses blood clots, exist in the form of a proenzyme, i.e. plasminogen. Fibrinolysis is generally agreed to be a normal process, potentially active at all times to insure the fluidity of blood and the patency of the vasculature. Because the formation of plasmin from plasminogen is an ongoing process in the body, the clinical determination of the fibrinolytic potential (e.g., as measured by plasminogen levels in blood or other body fluids) in a given individual is of great importance in the anticipation or treatment of systemic hyperfibrinolysis; post-surgical complications; neoplastic diseases such as carcinoma of the prostrate, lung, stomach and cervix; hemorrhagic states accompanying trauma; shock; liver disease and hematologic disorders; and thromboembolic phenomena in diabetes, atherosclerosis, venous stasis and thrombophlebitis.

Plasminogen can be activated in various ways to yield the active proteolytic enzyme, plasmin. For example, fibrinokinase activity has been found in many tissues and in the plasma and urokinase is obtained from the urine, while staphylokinase and streptokinase are obtainable from bacteria; all of these enzymes can activate plasminogen to form plasmin. Of these, urokinase is most widely employed in clinical practice today, in spite of its many inherent deficiencies. These are largely due to the very short (3–15 minutes) useful half-life of urokinase following its injection into humans, as has been reported by Fletcher et al. in J. Lab. Clin. Med. 65: 713 (1965). This short half-life is due to a number of factors. For example, the molecular weight of urokinase is below the threshold for kidney retention so that a substantial fraction of every administered does is therefore repidly lost by excretion into the urine. Furthermore, urokinase exists entirely in a form which is enzymatically fully active before injection; immediately upon injection, it reacts with the protease inhibitors that are normally present in relatively high concentrations in plasma and body fluids, and is thereby inactivated. The short in vivo half-life of urokinase requires frequent injections to achieve the desired therapeutic effect; this, together with the low concentrations of urokinase present in the urine and cell culture fluids that are the sources for preparing this enzyme, makes urokinase therapy very costly. Because of the widespread interest in plasminogen proactivator and activators, many attempts have been made to obtain plasminogen activators which do not share the above deficiencies of urokinase.

The use of streptokinase as a substitute for urokinase in such therapy is limited by the fact of its bacterial origin. Since streptokinase is a protein foreign to man, injection of streptokinase gives rise to the production of neutralizing antibodies which block its action and to allergic reactions that are harmful, and potentially fatal, to the recipient. Summaria et al., in J. Biol. Chem. 251 (18): 5810–5813 (Sept. 25, 1976) describe the isolation of a human plasmin-derived, functionally active human plasmin light (B) chain derivative which, mixed in equimolar amounts with streptokinase, develops both human and bovine plasminogen activator activities. However, this derivative is reported to possess only approximately 3% of the proteolytic activity of the original enzyme.

A number of earlier workers have described other combinations of plasminogen with streptokinase, resulting in an agent which possesses thrombolytic activities similar to streptokinase without reacting against antibodies thereto; for example, see Holleman et al., U.S. Pat. No. 3,865,692.

In another approach to overcoming the inherent deficiencies of streptokinase and urokinase as plasminogen activators, other investigators have turned their attention to obtaining plasminogen activators from different materials. For example, Wagner, U.S. Pat. No. 3,555,000, describes a plasminogen activator which can be isolated from the stromata of human erythrocytes and can be electrophoretically separated from urokinase. The activator is a water-soluble protein having a molecular weight of about 20,000–50,000 and which is itself activated by small amounts of urokinase.

Hull et al., U.S. Pat. No. 3,904,480, describe the culturing of another plasminogen activator from mammalian tissue culture cells, e.g. PK-15, LLC-MK$_2$, etc. This plasminogen activator is a water-soluble polypeptide having a molecular weight of approximately 30,000 and an activity, observed by the fibrin plate method and related to the optical density (OD) in the ultraviolet spectrum at 280 nm, of about 15,000–20,000 CTA units.

D'Hinterland et al., U.S. Pat. No. 3,998,947, describe a method for obtaining a plasminogen activator by acetone extraction of organ tissues, using a process similar to one which has long been employed in the preparation of organ tissue powders. The activator is endocellular and characterized as a glycoprotein having a molecular weight of approximately 40,000, containing from 300 to 500 CTA units per milligram and lacking esterase activity with respect to most, but not all, amino acid esters. The activator is medically useful in the treatment of arterial and venous thrombosis, and in the treatment of fibrinous deposits.

In spite of all the attempts at isolating new plasminogen activators, those heretofore employed in the prior art suffer from one or more deficiencies of limited purity and poorly reproducible potency; an extremely short half-life, thereby necessitating pharmaceutical administration by continuous slow injection, perfusion or the like, or frequent injections several times a day; susceptibility to inactivation by a number of chemicals commonly encountered in biological fluids; and induction of undesirable immunological reactions. In addition, the plasminogen activators that are prepared using tissues, extracted tissues or tissue powders as a starting material suffer from the disadvantage that they are present in very low concentrations and are accordingly difficult to purify and to obtain in reproducibly potent preparations. None of these deficiencies presently appears to apply to the newly isolated plasminogen proactivator and activator of the present invention.

OBJECTS OF THE INVENTION

Accordingly, it is a general object of the present invention to provide a new plasminogen proactivator (the enzymatically inactive precursor or proenzyme form) and its corresponding enzymatically active plasminogen activator.

Another object of this invention is to provide a method for isolating and purifying the novel plasminogen proactivator and activator from mammalian and avian plasma, plasma protein fractions and cell culture fluids, especially the human form.

A further object of the present invention is to provide pharmaceutical compositions and methods of use for the plasminogen proactivator and activator of the present invention.

Another object of the present invention is to provide antibodies directed against the newly isolated plasminogen proactivator and activator and methods for the application of these antibodies in the purification and detection of plasminogen proactivator and activator.

An additional object of the present invention is to provide an improved procedure for detecting proteolytic enzyme activity in plasma and other body fluids or tissue samples.

Upon further study of the specification and appended claims, further objects and advantages of this invention will become apparent to those skilled in the art.

SUMMARY OF THE INVENTION

Briefly, the above and other objects, features and advantages of the present invention are attained in one aspect thereof by providing an in vitro preparation of a plasminogen proactivator and activator which is isolated from mammalian or avian plasma or serum and is free of particulate cellular material and substantially free of other homologous serum proteins, i.e. which contains less than 5% and preferably less than 1% by weight thereof.

By virtue of the assay method described more particularly hereinafter, it has been found that normal human plasma contains about 15–30 mg/l. of plasminogen proactivator and activator, the vast majority of which is present in the proactivator form in the circulation. The two forms differ physically only by the latter's lacking a small portion of the polypeptide chain and therefore having a slightly lower molecular weight and probably different steric configuration. While also present in serum, the serum generally contains only a small fraction of the amount present in the plasma. The proteins are identical in charge and chromatographic behavior and each comprises two chains held together by disulfide bonds. While DFP irreversibly denatures this and other plasminogen activators, it has virtually no effect on the plasminogen proactivator of the present invention.

The serum plasminogen activator is electrophoretically a single, homogeneous protein, most of which is obtained in the inactive form requiring activation. It is structurally very similar to Plasma Factor XII but distinguishable in that it contains 1% methionine, and has the following properties:

A. comprising a single polypeptide chain containing the following amino acids in about the molar percentages shown:

| | | |
|---|---|---|
| 8–9% Aspartic | 5–6% Valine | 3.5–5% Lysine |
| 6 Threonine | 1 Methionine | 6–7 Arginine |
| 5–7 Serine | 1.5–2.5 Isoleucine | 5–6 Half-Cystine |
| 12–14 Glutamic | 9–10 Leucine | Tryptophane |
| 5–6 Proline | 3–4 Tyrosine | (qualitative) |
| 8.5–9.5 Glycine | 3–4 Phenylalanine | Glutamine |
| 8–10 Alanine | 5–6 Histidine* | Asparagine |

*greater than lysine

B. an elemental analysis which corresponds approximately to:
56.6% C; 7.1% H; 15.7% N; balance O and S;

C. a molecular weight, as determined by polyacrylamide gel electrophoresis in the presence of sodium dodecyl sulfate (SDS) and beta-mercaptoethanol, of about 92,000 daltons by reference to known standard proteins;

D. an ultraviolet spectrum with a characteristic peak at 280 nm;

E. being slightly soluble in water, aqueous ethanol and acetone but insoluble in lipophilic solvents;

F. being heat sensitive and becoming about 50% inactivated upon heating to 100° C. for 15 minutes;

G. being pH sensitive, having an optimal esterase activity against N-carbobenzoxy-L-lysine thiobenzoate at pH 8 and in general having esterase activity at pH 8 to 8.5 but becoming irreversibly denatured at pH 12 or higher;

H. being substantially free of immunochemical crossreactivity with antisera directed against human plasma kallikrein or human plasminogen;

I. being a protease which very efficiently activates human plasminogen to active plasmin by cleavage of a single bond in the plasminogen molecule, converting the single polypeptide chain of plasminogen to the two chains of plasmin; and J. the plasminogen activator, but not the proactivator, being irreversibly inactivated by diisopropyl fluorophosphate not significantly inhibited by either bovine pancreatic trypsin inhibitor (Kunitz) or soybean trypsin inhibitor (Kunitz).

DETAILED DESCRIPTION

It has now been found that a plasminogen proactivator and activator normally exist in and can be isolated from plasma, especially human plasma. According to a first aspect of the present invention, a plasminogen proactivator and activator is isolated from plasma and obtained as a single, homogenous species following purification thereof. Plasma containing a suitable anticoagulant, e.g. freshly citrated human plasma, is treated to remove extraneous protein, e.g. by precipitation with 1% polyethylene glycol having a molecular weight of about 6,000, barium chloride, or the like, and the precipitate discarded. The supernatant is then brought to partial saturation by the addition of solid ammonium sulphate, e.g. up to 50%, preferably about 35% saturation, and the precipitate which forms is separated by low-speed centrifugation and discarded. Sufficient additional ammonium sulphate is added to the supernatant to bring it to approximately 50% saturation, and the resultant precipitate collected by centrifugation, e.g. at 9,000 rpm for 15 minutes. The thus-obtained precipitate is dissolved in a minimal amount of water or buffer and desalted by dialysis, ion-exchange chromatography or gel filtration.

The resultant protein solution is further purified by sequential passage through a water-insoluble support, e.g. Sepharose, containing covalently bound L-lysine. A protease inhibitor e.g., 10 mM benzamidine hydrochloride, is added to the pooled flow-through protein solution. The protein solution containing plasminogen proactivator and activator is further purified by sequential passage through water-insoluble supports, e.g. Sepharose, containing, respectively, covalently bonded (a) soybean trypsin inhibitor; (b) basic pancreatic trypsin inhibitor; (c) DEAE (diethylaminoethyl); and (d) arginine. One or more of these four steps can be omitted, but with a great reduction in the final yield of plasminogen proactivator and activator. Optimal results have been obtained when the columns are run in the stated order.

The peak fractions containing the plasminogen proactivator and activator are then pooled, brought to a pH of about 5–7, preferably about pH 6.5, by the addition of a suitable inorganic mineral acid, e.g. phosphoric acid, and dialyzed against a suitable buffer at the same pH. Preferably, the buffering moiety has only a single group dissociating in the pH range of interest.

The fractions of interest are then adsorbed onto a column of previously equilibrated carboxymethyl sepharose. The column is washed successively with the adsorbing buffer and with a similar buffer containing 0.01 M NaCl, and the plasminogen proactivator and activator finally eluted with a similar buffer containing 0.2 M NaCl. Alternatively, plasminogen proactivator and activator is first concentrated after batchwise adsorption and elution from another column of carboxymethyl sepharose and further purified by gel filtration, e.g. over superfine Sephacryl S-200. The pooled peak fractions are dialyzed against N-morpholino ethane sulfonic acid, pH 6.0, the protein is adsorbed onto carboxymethyl sepharose and plasminogen proactivator and activator is eluted with a salt gradient (0.1–0.3 M NaCl in the equilibrating buffer). The peak fractions from this step are concentrated, e.g. by negative pressure dialysis or by dialysis against a saturated salt solution such as ammonium sulphate, and further purified by any of several known immunological, chemical or physical techniques for protein purification; such techniques include but are not limited to preparative polyacrylamide gel electrophoresis, hydrophobic chromatography and isoelectric focussing.

For example, preparative polyacrylamide gel electrophoresis containing sodium dodecyl sulphate such as described by U.K. Laemmli in Nature 227: 680 (1970) can be employed wherein the various peaks emerging from a column after 10 hours of electrophoresis (150 V, 45–16 ma) are collected and assayed for plasminogen activator activity.

Hydrophobic chromatography is preferably conducted on alkyl- or aryl-sephrose columns, e.g. phenyl-, octyl-, or butyl-sepahrose, adsorbing at high concentrations of salts (e.g. ammonium sulphate) and desorbing by decreasing salt concentrations and/or increasing concentrations of non-ionic detergents, e.g. Triton X-100, ethylene glycol, etc., e.g. as has been described by S. Hjerten et al. in J. Chromatography 101: 281 (1974). Iso-electric focusing is preferably effected as described by B. J. Radola in Ann. N.Y. Acad. Sci. 209: 127 (1973).

Immunological purification of the plasminogen proactivator and activator can be achieved from plasma obtained as described above or from any of the various plasma protein fractions containing the plasminogen proactivator and activator, e.g. Cohn fractions, preferably Cohn fraction IV-1. Either the plasminogen proactivator or the corresponding activator can be reacted with antibodies specific thereto, e.g. by precipitating antibodies. For other immunochemical diagnostic purposes, it has been found that the formation of an immunoprecipitating antigen-antibody complex between the plasminogen proactivator and activator and antibodies thereto will itself activate the proactivator, so that it is preferable to add a protease inhibitor to the reaction media. Preferably, an immobilized enzyme column to which specific antibodies have been covalently bonded or a sepharose column containing protein A (derived from streptococcus cell walls) to which immunoglobulins are specifically adsorbed is employed, since such a column adsorbs both the proactivator and activator forms with a high degree of specificity. After first washing with isotonic saline, both the proactivator and activator can be eluted from the column, e.g. with salt solutions such as 3 M KCNS or 1–2 M NaCl; with a low pH, e.g. pH 2–4; or with 4 M urea or 4–6 M guanidinium at neutral pH.

The protein is heat-sensitive, but retains its activity after being heated to 56° C. for 20 minutes. The plasminogen proactivator and activator exhibits good shelf storage stability at 4° C. and retains its activity upon freezing at −20° C. for 3 months in the presence of 10 mM benzamidine hydrochloride or in high concentrations of glycerol, e.g. about 50%. If desired, the plasminogen proactivator and activator can be lyophilized, preferably employing additives known to retard protein degradation, e.g. polyethylene glycol, bovine serum albumin and the like in normally employed concentrations. Lyophilized preparations exhibit substantially the same shelf stability as those which have been frozen, and show similar enzyme activity upon reconstitution to a protein concentration of about 0.1–1.0 mg/ml.

Using antibodies prepared against antigenically and physically pure plasminogen proactivator and activator as described herein, the diagnostic evaluation of human plasminogen proactivator and activator levels can be readily accomplished by standard radioimmunoassy (RIA) procedures, preferably using the solid-phase RIA technique of Catt et al. described in Acta Endocrinol. (Kbh) Suppl. 142: 222 (1969), the contents of which are incorporated by reference herein. For other immunochemical diagnostic purposes, it has been found that the formation of an immunoprecipitating antigen-antibody complex between the plasminogen proactivator and activator and antibodies thereto will itself activate the proactivator, so that it is preferable to add a protease inhibitor to the reaction media. Suitable such inhibitors are well known in the art and include but are not limited to those reported by Deutsch and Mertz in Science 170: 1095 (1970), the contents of which are incorporated by reference herein.

The implications resulting from being able to detect the circulating plasminogen proactivator in accordance with the present invention are substantial. For example, it has been found that under presently employed storage conditions blood bank blood loses most of the plasma plasminogen proactivator and activator during storage. By administering the proactivator of the present invention prior to, concurrently with or within hours of transfusing such blood, it is now possible to avoid decreasing plasminogen proactivator levels in the blood of patients to what appear to be dangerously low levels by the mere fact of transfusion to replace lost blood. While the proactivator can be added, e.g. at about 10 mg./l. to blood prior to transfusion thereof, this is not presently preferred. Because of its generally slow turnover rate in the body (only about 100 mg. per day), administration prior to surgery can often be sufficient for the next several days, depending on the dosage selected. The physician need merely determine circulating plasminogen proactivator levels in the healthy patient, estimate the patient's blood volume lost or replaced, and administer sufficient plasminogen proactivator to restore the circulating levels thereof to normal.

The compounds of this invention are generally administered to animals of the same or immunologically related species from which the plasminogen proactivator and activator have been obtained, including but not limited to birds and mammals, e.g. poultry, livestock, household pets, humans, cattle, cats and dogs. A suitable thrombolytically effective initial dosage of the active compounds as administered parenterally to humans can be readily calculated from knowledge of the patient's actual plasminogen activator levels and the desired level to be achieved, taking into account estimated blood volume; this generally comprises about 100 to 5,000, preferably 300 to 1,500 mg. per kg. of body weight together with 1–500 mg. of pharmaceutically acceptable carrier. The dose can be administered singly or as divided dosages throughout the day, but is generally administered singly since, due to the relatively long useful life of the plasminogen proactivator in the bloodstream, dosages may not require administration more often than daily, frequently only weekly and occasionally only monthly.

The compounds of this invention can be employed, either in pure or in a physiologically acceptable, non-toxic impure form such as Cohn Fraction IV-1, in mixture with convention parenteral excipients, i.e. pharmaceutically acceptable organic or inorganic carrier substances suitable for parenteral application which do not deleteriously react with the active compounds. Suitable pharmaceutically acceptable carriers include but are not limited to water, salt solutions, alcohols, polyethylene glycols, gelatine, lactose, amylose, etc. The pharmaceutical preparations can be sterilized and if desired mixed with auxiliary agents, e.g. preservatives, stabilizers, wetting agents, emulsifiers, salts for influencing osmotic pressure, buffers, coloring, flavoring and/or aromatic substances and the like which do not deleteriously react with the active compounds. Sterilization is best achieved by sterile filtration through filters, such as Millipore filters, of small pore size (0.45 micron diameter or smaller), after which the preparations can be lyophilized, if desired. In addition, a variety of antibiotics may be added to assist in preserving sterility.

Parenteral administration is generally required, the plasminogen activator of this invention being particularly valuable in the treatment of humans whose circulating level of plasminogen activator is decreased, e.g. as in certain cases of diabetes, atherosclerosis, prolonged immobilization, major surgery, trauma, multiple blood transfusions and other diseases predisposing to thromboembolic and other occlusive phenomena. In addition, it may be used in fibrinolytic therapy of established or incipient thrombi and can be employed in substantially the same manner as the known compound urokinase, taking into account the differences in properties described herein.

For parenteral application, particularly suitable are solutions, preferably oily or aqueous solutions, as well as suspensions, emulsions or implants, including suppositories. Ampoules are convenient unit dosages.

Generally, the compounds of this invention are dispensed in unit dosage form comprising 1–5000 mg. of a pharmaceutical carrier per each unit dosage and the amount of active agent of the invention per unit dosage is generally about 10 to 200 mg., preferably about 20 to 100 mg.

It will be appreciated that the actual preferred amounts of plasminogen proactivator and activator used will vary according to the specific preparation being utilized, the particular compositions formulated, the mode of application, and the particular situs and organism being treated. Optimal application rates for a given set of conditions can be ascertained by those skilled in the art using conventional dosage determination tests in view of the above guidelines.

The combination of procedures described herein, whereby reaction mixtures or biological fluids are first analyzed by SDS-PAGE (sodium dodecyl-sulfate polyacrylamide gel electrophoresis) and then evaluated by digestion of fibrin-agar gels, is of general usefulness for detecting and identifying proteases and zymogens of the "serine enzyme" type, particularly those that are active in extracellular milieu.

To retain the advantages of SDS-PAGE under conditions permitting more rapid, precise and economical detection of proteases, we have applied the method of Converse and Papermaster described in Science 189: 469 (1975) and have used solutions of non-ionic detergents for extracting SDS after completion of electrophoresis. This procedure efficiently removes SDS but does not extract significant quantities of protein; the electrophoretic slab gel can then be layered onto a second indicator gel comprising fibrin and agar. Zones of fibrin degradation, corresponding to the position of proteases in the SDS-gel overlay, can be seen as clear areas in an opaque background on dark field illumination, or as clear areas in a dark blue background following fixation and staining with Coomassie blue or amido black.

The method is sensitive, permitting the detection of nanogram amounts of proteases in less than 1 microliter of fresh plasma. The fibrinolytic zones formed in the indicator gel are sharp and narrow and permit small differences in electrophoretic mobility, e.g. molecular weight differences of the order of 2,000, to be resolved. The procedure can readily be made quantitative, provided that it is appropriately standardized and calibrated by reference to known amounts of the enzyme under study. The method is useful for monitoring the fractionation of specific proteases during purification and chromatography.

With minor modifications appropriate to each particular system, e.g. the substitution of fibrin by casein, hemoglobin or other chromoproteins which can provide better substrates for individual proteases, this procedure has been applied to a broad spectrum of serine enzymes and proenzymes. For example, plasminogen can be identified in the electrophoretic gel by reversing the conditions used for locating plasminogen activators, that is, by incorporating a plasminogen activator (e.g. human urokinase) into the fibrin-agar underlay. This approach is useful for detecting plasminogen at concentrations below those required for activation in free solution (i.e., below $K_m$ for activators), since electrophoresis in gradient gels crowds the molecules into narrow bands and provides a high local concentration permitting efficient activation. Proteases such as trypsin, chymotrypsin and elastase hydrolyze fibrin directly and they are easily detected by using plasminogen-free fibrin-agar indicators. By substituting fibrinogen for fibrin, supplementing the indicator gel with appropriate co-factors and observing the reaction under dark-field illumination, it is possible to use clotting rather than fibrinolysis as an end-point and thereby to locate enzymes of the coagulation pathway using this method.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. All temperatures are set forth uncorrected in degrees Celsius; unless otherwise indicated, all pressures are ambient and all parts and percentages are by weight. The values obtained by elemental analysis are within the usual limits of experimental error.

EXAMPLE 1

Preparation of Purified Plasminogen Activator

Fresh citrated human plasma containing 57.5 g. protein per liter is treated with $BaCl_2$ (200 meq. of $BaCl_2$ per liter of plasma) and the precipitate discarded. The supernatant is brought to 35% saturation by the addition of 19.4 g/100 ml solid ammonium sulfate and the precipitate which forms is separated by centrifugation and discarded. An additional 8.7 g/100 ml solid ammonium sulfate is added to the supernatant to achieve 50% saturation, and the resulting precipitate is collected by centrifugation at 9000 rpm for 15 minutes. The precipitate is dissolved in a minimum amount of phosphate buffer (0.05 M, pH 8.0) and desalted by passage through a column of Sephadex G-25, previously equilibrated with phosphate buffer (0.05 M, pH 8.0).

The pooled protein peak is passed through a column containing Sepharose with covalently bound L-lysine (50 ml) equilibrated with phosphate buffer (0.05 M, pH 8.0). To the flow-through protein peak containing plasminogen proactivator and activator (total protein=7.2 g), benzamidine hydrochloride was added to a final concentration of 10 mM.

The pooled protein solution is sequentially passed through (a) a "Trasylol" (bovine basic pancreatic trypsin inhibitor)—sepharose column; (b) a soybean trypsin inhibitor—sepharose column, (c) a DEAE (diethylaminoethyl)—sepharose column; and (d) an arginine—sepharose column. The flow-through protein peaks contained the plasminogen proactivator and activator (total protein=5.6 g).

The protein solution is adjusted to pH 6.5 by the addition of phosphoric acid. The solution is then passed through a carboxymethyl sepharose column (50 ml) equilibrated with 0.05 M phosphate buffer, pH 6.5, containing 10 mM benzamidine hydrochloride. The column is successively washed with 50 mM, 100 mM and 200 mM NaCl in 50 mM phosphate buffer, pH 6.5, containing 10 mM benzamidine hydrochloride. The adsorbed plasminogen proactivator and activator is eluted by a 0.2 M NaCl solution (total protein=9.6 mg).

The protein solution is concentrated by dialysis against a saturated $(NH_4)_2SO_4$ solution in 0.1 M Tris-Cl, pH 8.0, containing 10 mM benzamidine hydrochloride. The precipitate containing plasminogen proactivator and activator is collected by centrifugation (15,000 rpm, 15 minutes) and dissolved in 1-2 ml of 0.1 M Tris-Cl, pH 8.0, containing 0.5 M NaCl and 10 mM benzamidine chloride. The concentrated protein solution was then applied to a Sephacryl S-200 column for gel filtration. The active protein peak is pooled and dialyzed against 5 mM N-morpholino ethane sulfonic acid containing 10 mM benzamidine hydrochloride (total protein=2.7 mg).

The protein solution containing plasminogen proactivator and activator is then applied to a carboxymethyl-sepharose column (5 ml in 0.01 MES, pH 6.0, 10 mM benzamidine hydrochloride). The adsorbed plasminogen proactivator and activator is eluted with a gradient of NaCl (0.1 M to 0.3 M) to yield a total protein=1.5 mg. The purified plasminogen proactivator and activator is essentially homogeneous in sodium dodecyl sulfate (SDS) polyacrylamide gel electrophoresis.

EXAMPLE 2

Alternate Purification

Following the procedure of Example 1, purification of plasminogen proactivator and activator is also achieved by omitting sequential passage of pooled protein through Sepharose covalently bonded to bovine basic pancreatic trypsin inhibitor, soybean typsin inhibitor, DEAE and arginine. The overall yield of active protein is about 60% less than that obtained from following the complete procedure of Example 1.

EXAMPLE 3

Electrophoretic Purification

Following the procedure of Example 1, the plasminogen proactivator and activator is purified by preparative polyacrylamide gel electrophoresis containing sodium dodecyl sulfate in place of the last adsorption and elution from carboxymethyl-sepharose. The various peaks emerging from the gel column after a period of electrophoresis lasting 10 hours (150 V, 45-16 ma) are collected and assayed for plasminogen proactivator and activator activity. The peak containing the proactivator and activator can be further characterized for purity, homogeneity, etc. by standard procedures.

The molecular weights of plasminogen activator and proactivator were determined by SDS-PAGE using gels containing 10% polyacrylamide and 0.1% sodium dodecyl sulfate. The procedures were performed under both non-reducing conditions and under reducing conditions in the presence of 5% beta-mercaptoethanol. Electrophoresis was at constant voltage (45 V) for approximately 16-18 hours at room temperature. The molecular weights of standard marker proteins were 14,000; 28,000; 42,000; 56,500; and 71,500 in both reduced and non-reduced gels. Using a standard calibration curve for each set of conditions, the molecular weight for single chain plasminogen proactivator was 92,000 under non-reducing conditions and 80,000 under reducing conditions. The plasminogen activator, consisting of two polypeptide chains, was indistinguishable from the proactivator under non-reducing conditions; the individual chains had molecular weights of about 58,000 and 34,000 under reducing conditions. As controls, human plasminogen migrated as two bands with apparent molecular weights of 100,000 and 94,000, respectively, while human kallikrein migrated with a molecular weight of about 102,000.

EXAMPLE 4

Preparation of Antibodies

Using the antigenically and physically pure plasminogen proactivator and activator prepared as described in Example 1, rabbit antibodies thereto were prepared by the following inoculation schedule. Dosages of 1 mg/ml plasminogen proactivator and activator obtained from preparative electrophoresis in gels containing 0.1% of SDS protein measured according to Lowry et al., J. Biol. Chem., 193: 265 (1951) were administered to rabbits using a vaccine comprising a solution of plasminogen proactivator and activator with Fruend's complete adjuvant and administered to the animals via subcutaneous, intramuscular, peritoneal and foot pad injections. Injections were given on days 0, 7, 14, 21 and 28 and the animals rested for a period of 7 weeks, after which a booster injection was given and blood samples drawn 1, 2, 3 and 4 weeks thereafter. The rabbit blood was worked up conventionally by allowing it to clot and the antisera collected by centrifuging to remove the precipitated clot. Similar results are obtained by injecting larger mammals such as sheep, goats, pigs and horses.

EXAMPLE 5

Purification from Cohn Fractions

A. Plasminogen proactivator and activator was also purified from Cohn Fraction IV-1 prepared from human plasma. Cohn fraction IV-1 (frozen, paste) was extracted twice with salt solution (0.6 M NaCl). The suspension was centrifuged and the supernatant from both extractions is combined. The supernatant is adjusted to pH 2.2 with phosphoric acid and allowed to stand for 30 minutes. The solution is then neutralized with 1.0 M NaOH to about pH 7.6. Sodium phosphate buffer pH 7.6 was added to bring the final concentration to 10 mM with respect to buffer and 0.15 M with respect to salt. The solution was then passed through an immobilized soybean trypsin inhibitor column. The flow-through solution thus obtained contains most of the plasminogen proactivator and activator activity. Protease inhibitor (e.g. 10 mM benzamidine chloride) was added immediately to the pooled solution; this served as the starting material for further purification following the method described in Example 1 except that passages thru covalently bound L-lysine and the following four sequential columns were eliminated.

B. Following the procedure of Example 5 but starting with 250 g of Cohn fraction IV-1, about 10 mg of essentially pure plasminogen proactivator and activator was obtained. The acidification step was not essential.

EXAMPLE 6

Radioimmunoassay

Plasminogen activator was assayed using the $^{125}I$-fibrin plate method described in Cell 8:271 (1976). One unit of enzyme was defined as the amount that catalyzed the solubilization of 5% of the total radioactivity in 2 h under standard conditions.

Gels and buffers for SDS polyacrylamide gel electrophoresis were prepared according to Laemmli in Nature. London 227: 680 (1970). Slab gels (9×15 cm) with stacking gels of 4% acrylamide were used. Samples contained a final concentration of 2.5% SDS. Electrophoresis was performed at constant current (8 ma) until the dye front reached the bottom of the gel, approximately 18 h. After completion of the run the gel was sliced longitudinally between the appropriate lanes and washed, by gentle rocking for 1 h, in a solution of 1.5% (w/v) Triton x-100 or Lubrol PX. The gel was then rinsed thoroughly with distilled water and applied to the surface of a fibrin-agar indicator gel.

The fibrin-agar gels were prepared using the following solutions: (a) a 2.5% solution of agar in water, boiled for 10 minutes prior to use and kept at 42° C.; (b) PBS (phosphate buffered saline) supplemented, where desired, with plasminogen (18 micrograms/ml) and thrombin (0.2 U/ml), warmed to 42° C.; and (c) fibrinogen (10 mg/ml) in PBS. 3.2 ml of solution (a) was added to 1.9 ml of solution (b) and, after mixing, 1.3 ml of solution (c) was added. The solutions were mixed rapidly and then poured into the plastic covers (14×9 cm) of Linbro multi well dishes, care being taken to avoid bubbles. The solution was spread evenly on the surface of the dish, allowed to form a firm gel and used immediately.

The washed electrophoretic gel was laid carefully onto the indicator gel, the unit sealed with plastic wrap and incubated at 37° C. in a humid environment. At intervals the plates were removed for observation in a Dade dark-field immunodiffusion viewer. The lysis zones were easily seen as clear areas in the cloudy background provided by the unlysed fibrin. Depending on the concentration of enzyme in the electrophoretic gel, lysis zones may become visible at times ranging from 1–36 h. After the reaction had progressed to the desired extent, the electrophoretic gel was removed, the fibrin layer was stained for 10 min with a solution containing 0.1% amido black in 70% methanol, 10% acetic acid and destained in 70% methanol, 10% acetic acid. Alternatively, gels were also stained with 0.25% Coomassie brilliant blue in 50% methanol, 7% acetic acid and destained in 30% methanol, 10% acetic acid.

For quantitative comparison of proteolytic activity, washed electrophoretic gels were placed onto fibrin-agar gels that had been coated on the surface of glass slides (2×14 cm). These slides were incubated as described above for coated plastic surfaces. After appropriate incubation the polyacrylamide gel was removed, the fibrin-agar gel fixed with destaining solution and dried. The lysis zone was then analyzed by densitometry in a Joyce-Loebl Model E12 MK3 densitometer, and the size of the peak was measured by cutting out the area on the graphic representation of the scan and weighing it.

EXAMPLE 7

Plasminogen Activator Screening

The gel assay procedure described in Example 6 was modified for screening the plasminogen activator content of large numbers of samples and for unmasking cryptic or inhibited forms of the enzyme. To identify plasminogen activators, duplicate SDS-gels were tested on two fibrin-agar indicators, one of which had been supplemented with plasminogen. Even for crude samples of unpurified urine and cell culture fluids, the presence of plasminogen permits the development of distinct zones of lysis. For all of the samples tested no lytic bands were observed in the absence of plasminogen, indicating that the major source of SDS-resistant proteolytic activity in these fluids was due to plasminogen activator. Several bands of plasminogen activator were present in each specimen (4 or 5 for the human having an average isoelectric point of about 7.1), and the molecular weights of the human enzymes differed significantly from those of rodent species. In general, the predominant molecular weights from the plasminogen activators found in cell culture media were lower than those of the plasma enzymes from the same species, suggesting that the cell culture enzymes might be partial degradation products derived from a larger molecule.

The spectrum of plasminogen-dependent and independent proteolysis was somewhat different in plasma from various species. Both types of indicator gels revealed multiple bands, showing the presence of plasminogen activators as well as other proteases whose electrophoretic mobilities placed them in the same region of the gel. Detailed analysis of these patterns for human plasma has shown that all of the plasminogen-independent lytic zones were due to different electrophoretic forms of plasmin, whereas the plasminogen-dependent lysis was produced either by a newly isolated plasminogen activator or, occasionally, by kallikrein.

EXAMPLE 8

Radioimmunoassay

Because the method yields an estimate of molecular weight for each band of proteolytic activity detected, it appears to be advantageous for analysing some properties of complexes formed between proteases and various inhibitors, especially those found in plasma. Examples of such applications to the complexes involving alpha-macroglobulin (alpha$_{2M}$) and trypsin or plasmin, respectively, have been successfully performed.

In these experiments the proteases were first labeled with $^{125}$I to permit their detection by autoradiography, and then reacted with alpha$_2$-macroglobulin; several aliquots of each reaction were subjected to SDS-PAGE and duplicate lanes from the gels were then analysed further, either by autoradiography to locate all labeled species or by fibrin-agar gels to identify those that retained proteolytic activity. The two patterns thus obtained revealed the following:

(a) in each reaction mixture multiple forms of enzyme were separated by SDS-PAGE. For both plasmin and trypsin there were several distinct bands in the very high molecular weight region of the gel, corresponding to the position of the alpha$_2$-macroglobulin, and some radioactivity migrated at a rate indistinguishable from the free, uncomplexed enzymes.

(b) comparison of autoradiographic and fibrinolytic patterns showed that essentially all of the autoradiographically detectable forms of plasmin were catalytically active. Since it is known that native plasmin-alpha$_{2M}$ complexes do not hydrolyse macromolecular substrates, exposure to SDS may have denatured portions of the inhibitor structure and abolished any steric obstruction to the interaction between alpha$_{2-M}$-complexed plasmin and proteins such as fibrin.

(c) the patterns found with trypsin resembled those observed with plasmin, but they differed in one respect: the high molecular weight trypsin-alpha$_{2M}$ complexes were catalytically inactive after SDS-PAGE, suggesting the persistence of some structural restraints that blocked the action of complexed trypsin on fibrin. However, brief exposure of trypsin-alpha$_{2M}$ complexes to low pH prior to SDS-PAGE abolished these restraints and unmasked the proteolytic activity of bound trypsin. Addition of excess trypsin led to partial degradation of the trypsin-alpha$_{2M}$ complexes, yielding forms intermediate in molecular weight between free enzyme and enzyme-alpha$_{2M}$ complexes; these also retained proteolytic activity.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

What is claimed is:

1. An in vitro preparation of a plasminogen proactivator which is capable of being isolated from human plasma or serum and is free of particulate cellular material, characterized by having the following properties:

A. comprising a single polypeptide chain containing the following amino acids in about the molar percentages shown:

| | | |
|---|---|---|
| 8–9% Aspartic | 5–6% Valine | 3.5–5% Lysine |
| 6 Threonine | 1 Methionine | 6–7 Arginine |
| 5–7 Serine | 1.5–2.5 Isoleucine | 5–6 Half-Cystine |
| 12–14 Glutamic | 9–10 Leucine | Tryptophane |
| 5–6 Proline | 3–4 Tyrosine | (qualitative) |
| 8.5–9.5 Glycine | 3–4 Phenylalanine | Glutamine |
| 8–10 Alanine | 5–6 Histidine* | Asparagine |

*greater than lysine

B. an elemental analysis which corresponds approximately to: 54.6% C; 7.1% H; 15.7% N; balance O and S;

C. a molecular weight, as determined by polyacrylamide gel electrophoresis in the presence of sodium dodecyl sulfate (SDS) and beta-mercaptoethanol, of about 92,000 daltons by reference to known standard proteins;

D. an ultraviolet spectrum with a characteristic peak at 280 nm;

E. being slightly soluble in water, aqueous ethanol and acetone but insoluble in lipophilic solvents;

F. being heat sensitive and becoming about 50% inactivated upon heating to 100° C. for 15 minutes; and G. being substantially free of immunochemical cross-reactivity with antisera directed against human plasma kallikrein or human plasminogen H. being substantially uneffected by diisopropyl fluorophosphate.

2. A composition according to claim 1 which contains less than 5% by weight thereof of other homologous serum proteins.

3. An in vitro preparation of a plasminogen activator which is capable of being isolated from human plasma or serum and is free of particulate cellular material, characterized by having the following properties:

A. comprising a single polypeptide chain containing the following amino acids in about the molar percentages shown:

| | | |
|---|---|---|
| 8–9% Aspartic | 5–6% Valine | 3.5–5% Lysine |
| 6 Threonine | 1 Methionine | 6–7 Arginine |
| 5–7 Serine | 1.5–2.5 Isoleucine | 5–6 Half-Cystine |
| 12–14 Glutamic | 9–10 Leucine | Tryptophane |
| 5–6 Proline | 3–4 Tyrosine | (qualitative) |
| 8.5–9.5 Glycine | 3–4 Phenylalanine | Glutamine |

-continued

| 8-10 Alanine | 5-6 Histidine* | Asparagine |

*greater than lysine

B. an elemental analysis which corresponds approximately to: 54.6% C; 7.1% H; 15.7% N; balance O and S;
C. a molecular weight, as determined by polyacrylamide gel electrophoresis in the presence of sodium dodecyl sulfate (SDS) and beta-mercaptoethanol, of about 92,000 daltons by reference to known standard proteins;
D. an ultraviolet spectrum with a characteristic peak at 280 nm;
E. being slightly soluble in water, aqueous ethanol and acetone but insoluble in lipophilic solvents;
F. being heat sensitive and becoming about 50% inactivated upon heating to 100° C. for 15 minutes;
G. being pH sensitive, having an optimal esterase activity against N-carbobenzoxy-L-lysine thiobenzoate at pH 8 and in general having esterase activity at pH 8 to 8.5 but becoming irreversibly denatured at pH 12 or higher;
H. being substantially free of immunochemical cross-reactivity with antisera directed against human plasma kallikrein or human plasminogen;
I. being a protease which very effectively activates human plasminogen to active plasmin by cleavage of a single bond in the plasminogen molecule, converting the single polypeptide chain of plasminogen to the two chains of plasmin; and
J. being irreversibly inactivated by diisopropyl fluorophosphate but not significantly inhibited by either bovine pancreatic trypsin inhibitor (Kunitz) or soybean trypsin inhibitor (Kunitz).

4. A composition according to claim 3 which contains less than 5% by weight thereof of other homologous serum proteins.

* * * * *